United States Patent
Reifel et al.

(10) Patent No.: US 8,436,329 B2
(45) Date of Patent: May 7, 2013

(54) SYSTEM AND METHOD FOR FLUID SAMPLE ANALYSIS HAVING A LASER WITH A PORT FOR CONTROLLING ACCESS TO AN EXTENDED CAVITY

(75) Inventors: Michael Dean Reifel, Sugar Land, TX (US); Mitchell Hayes Reifel, Irvine, CA (US)

(73) Assignee: AMR Trust, Pearland, TX (US)

( * ) Notice: Subject to any disclaimer, the term of this patent is extended or adjusted under 35 U.S.C. 154(b) by 328 days.

(21) Appl. No.: 13/021,659

(22) Filed: Feb. 4, 2011

(65) Prior Publication Data

US 2011/0197654 A1    Aug. 18, 2011

Related U.S. Application Data

(60) Provisional application No. 61/304,409, filed on Feb. 13, 2010.

(51) Int. Cl.
*G01N 15/06* (2006.01)

(52) U.S. Cl.
USPC .......................................... 250/573; 250/239

(58) Field of Classification Search .......... 250/573–576, 250/239, 238, 227.14, 227–19, 227.25; 372/92–96, 372/50.11, 50.121, 23.2–23.36; 600/459, 600/476, 310

See application file for complete search history.

(56) References Cited

U.S. PATENT DOCUMENTS 4,452,533 A * 6/1984 Miles et al. ................... 356/506

\* cited by examiner

*Primary Examiner* — Que T Le
(74) *Attorney, Agent, or Firm* — Kevin M. Jones

(57) ABSTRACT

A LASER based system for analysis of fluids utilizing frequency shift analysis. In the preferred embodiment of the invention, the liquid for analysis is reduced to a gaseous state so that it can be injected into an extended LASER cavity, so as to detect minute frequency shifts caused by the various gases in the cavity via sensors associated with the cavity. The present invention thereby provides stable detection system, with microprocessor-based electronics, which can be used to provide analyses of the gases, and thus the input liquids and its markers.

20 Claims, 2 Drawing Sheets

17 Laser Cavity
18 Input Controls/Data Analysis

ERS/Mirror 20
21 Extended Cavity
19 Silicon Monoxide Coating
17 Laser Cavity
18 Input Controls/Data Analysis

SYSTEM AND METHOD FOR FLUID SAMPLE ANALYSIS HAVING A LASER WITH A PORT FOR CONTROLLING ACCESS TO AN EXTENDED CAVITY

CROSS-REFERENCE TO RELATED APPLICATIONS

This application claims priority under 35 U.S.C. §119(e) from U.S. Provisional Patent Application No. 61/304,409, by Michael Dean Reifel, et al. "System for Fluid Sample Analysis", filed Feb. 13, 2010 which is incorporated by reference for all purposes.

BACKGROUND OF THE INVENTION

The present invention relates to a system for fluid analysis utilizing a LASER device having sensors utilizing a change in operating frequency to analyze various compounds.

DETAILED DESCRIPTION OF THE PREFERRED EMBODIMENTS

Figure 1:
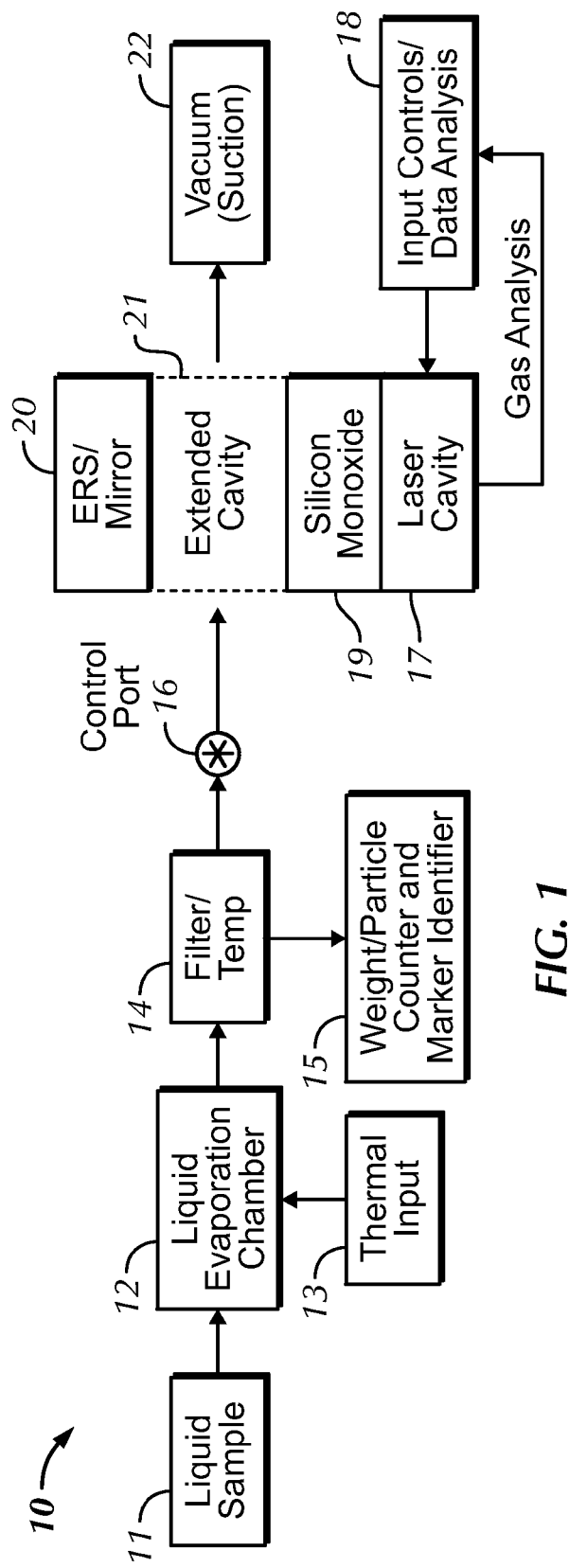
FIG. 1 illustrates block diagram of the system for fluid sample analysis in accordance with an exemplary embodiment of the invention

In the preferred embodiment of the invention, a liquid for analysis is reduced to a gaseous state, then filtered to remove desired particles/impurities, providing a filtered gas. The filtered gas is then injected into an extended cavity where it is illuminated by a LASER, where sensors are employed so as to detect minute changes in operating frequency caused by the various gases in the cavity. The present invention thereby provides a stable detection system, with microprocessor-based electronics, which can be used to provide analyses of the gases, and thus the input liquids and its markers.

Referencing the drawings, the present apparatus sets forth a LASER body, comprising a solid body of active material capable of lasing action, wherein the body is cooperative with two or more reflective surfaces, or mirrors, configured to encode measured information from the beam emitted from the LASER. The reflectivity of the mirrors is positioned and adjusted to receive the beam that is emitted from a selected end face or faces of the body of lasing material. Moreover, a separate or remote (external) reflective mirror can also be included, for example, installed parallel to the faces of the LASER body. This external reflective mirror may be positioned so as to direct the LASER beam from a remote point back into the body, for modification of the coherent beam generation occurring in the body.

There is a space or gap established between the LASER body and external mirror, the space or gap enabling the mirror to be affixed remote from the lasing body. This spacing for mirror and LASER body creates an extended LASER cavity, and enables the geometry of the measuring device to be modified for the development of all types of measuring devices (such as that described in U.S. Pat. No. 4,983,035, entitled "Laser Measuring Devices", the disclosure of which is incorporated here by reference) that allow encoding of measurements on the LASER frequency.

The purpose of the current apparatus is to fix the extended cavity geometry, or be able to calibrate for changes, so that gases can be introduced into the space or gap established between the LASER body and external mirror, thereby allowing encoding of measurements of the gases affects on the LASER frequency. Each gas or mixture of gases will cause the extended LASER cavity to operate at a separate and unique frequency, i.e., the standing wave pattern that can be supported by the cavity is a function of the cavity length [$\mathcal{L}$] and gas mixture at any given instant and all other wave patterns will collapse. The LASER device input can be cycled so that the LASER is fast-tuned until the devise stabilizes at (locks onto) a specific frequency, all of which occurs almost instantaneously.

The LASER beam is thus generated within the cavity comprised of lasing material, is directed out one end face thereof, is transmitted through a distance (or space) to be reflected from the external mirror, and is directed back into the LASER body. This reinforces the beam generation occurring in the LASER body which thereby defines coherent beam formation and beam frequency which is emitted out of the LASER body. The emitted beam is then directed either from the second face of the body, or from the external mirror, encoding the measurement of the gases and any changes in the component spacing [$\mathcal{L}$]. Physical changes in the component spacing can be controlled by material selection, and calibrated with temperature monitoring techniques, which are well known (such as that described in U.S. Pat. No. 4,930,134, entitled "Precision Temperature Sensor", the disclosure of which is incorporated here by reference).

All known pure gases, and various mixtures thereof, can be injected into the LASER's extended cavity and the frequency coded information for each gas or mixture can be stored in an electronic library associated with the device's control system. When an unknown gas, or mixture, is run through the extended cavity, it will be identified instantaneously.

To analyze liquids, such as blood, urine, or other unknown substances, biomarkers and other materials present in the liquid must first be prepared for gas analysis. A burst from a temperature LASER (or other heat source) will vaporize the liquid and its components, which will then be filtered to remove any remaining solids, before the remaining gas is injected into the extended cavity. The vaporizing temperature can be varied in order to reserve certain expected solids that can be counted, weighed, and identified from the filtration unit. Or, the temperature burst can be high enough so that all liquid and solid components therein, are vaporized. The gas temperature can be reduced or increased, according to the gaseous state before being injected into the extended cavity, so that the mixture can be calibrated accordingly.

Although blood and urine were listed examples of liquid samples in the preceding paragraph, one skilled in the art will understand that many other liquids, beyond bodily fluids, can be analyzed using the techniques describe here. Other examples may include, but should not be limited to water, plant juices, oils, etc. Further, it should be apparent a liquid sample may actually be a semi-liquid, gel, or even a substantially solid material with high moisture content. An example may include bodily tissue, which have high moisture content. One skilled in the art would understand that this could also include plant and animal tissues as well.

Attention is first directed to FIG. 1 which illustrates block diagram of the system for fluid sample analysis of blood, or any other liquid 10. The analysis is made by a semiconductor LASER 17 as part of an integrated circuit that is controlled by microprocessor-based electronics 18. While FIG. 1 shows the preferred embodiment, using a semiconductor LASER 17, other forms of LASER, including gas, can be used. The system will be described in the context of analyzing a sample of blood as a first example of the mode of operation of the device, but any other liquid 11 could also be analyzed.

For the present example, the sample for analysis is one cc (1 cc) in size and contains a whole blood compound with all fluids and biomarkers (such as protein molecules) that indicate the presence of physiological conditions. It could also be any unknown liquid compound, of any size suitable for processing. The blood sample 11 is inserted in an evaporation chamber 12 and subjected to a temperature burst from a variable thermal source 13, such as ultraviolet light or other. This thermal source 13 could be a variable controlled LASER, or conventional electrical device with variable controls. The specific temperature burst will be a factor of the profile of the blood compounds sought. As an alternative, 100% of the liquid sample, with all compounds, could be transformed to a gaseous state.

The LASER 17 with its extended cavity (EC) 21 is initially in a vacuum created by a Vacuum or Suction device 22. Entry to the EC is controlled by a control port 16. This state allows the LASER control system 18 to establish the fundamental operating frequency of the controlled extended-LASER cavity sub-system, which information is used in the input control and analysis processes.

When the control port 16 is opened, the gases and compounds in the evaporation chamber 12 are drawn (via the vacuum, for example) into the filter/temperature control unit 14, which removes all solid compounds and debris, as the clean gases are drawn into the extended cavity 21. Some gases may require a temperature burst from the filter/temperature control unit 14 to remain in a gaseous state. The solids from this unit 14 can be counted and weighed for certain physiological information by use of a Weight/Particle Counter & Marker Identifier 15. Solids of this nature are commonly referred to as 'particles' in the oil and gas industry. Solids of this nature are commonly referred to as 'markers' in the medical industry. Other industries may use different terms. Depending on the type of solids, which ultimately depends on the type of sample, physiological information can be obtained from differing types of analysis of deterministic properties. In one embodiment the weight of the solids may be deterministic. In another embodiment the type of solids may be deterministic. In another embodiment the numbers or volume of solids may be deterministic. In another embodiment a combination of multiple factors may be deterministic. One or more devices may be used, alone or in combination to access this physiological information.

Figure 2:
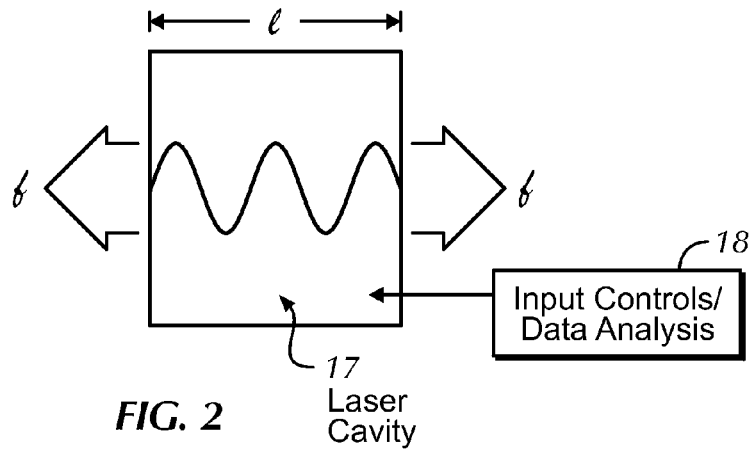
FIG. 2 illustrates a schematic diagram of a semiconductor LASER used for analysis in accordance with an exemplary embodiment of the invention.

FIG. 2 illustrates a schematic diagram of a semiconductor LASER used for analysis in accordance with an exemplary embodiment of the invention as illustrated in FIG. 1, further illustrating an exemplary LASER cavity [l] and first and second beam emissions therefrom.

Attention is directed to FIG. 2 of the drawings where the preferred semiconductor LASER 17 is a Gallium-Aluminum-Arsenide (GaAlAs) device with a cavity length [l], of about 300 microns, operating at a wavelength of about 8400 Angstroms. One skilled in the art of LASERS and their use will understand that the exact cavity length and operating wavelengths will vary with the manufacturing process and coating. However, the exact dimensions are not critical to the operations described, as long as an accurate calibration is performed as taught herein this specification. The LASER is typically constructed so that it emits light out of both ends.

Figure 3:
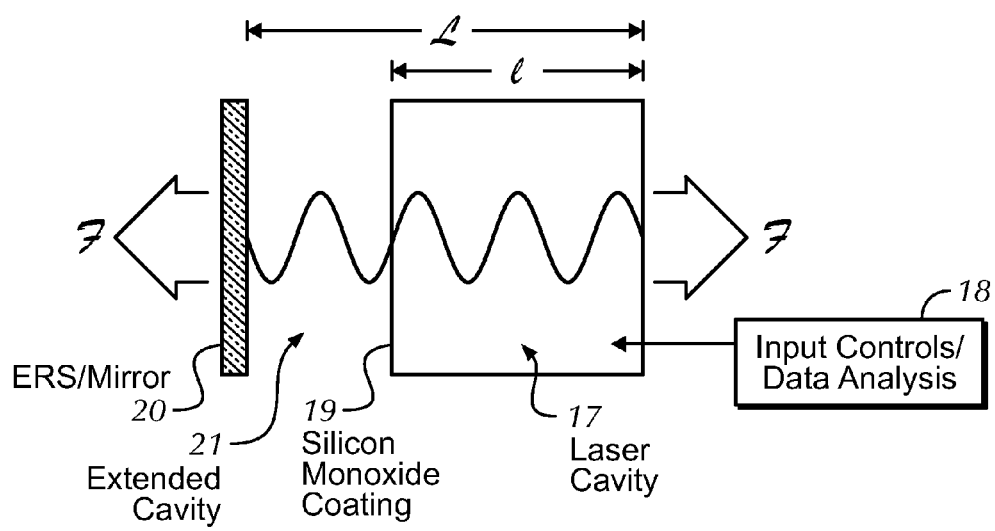
FIG. 3 illustrates a schematic diagram illustrating a LASER with extended cavity used for analysis in accordance with an exemplary embodiment of the invention.

FIG. 3 illustrates a schematic diagram illustrating a LASER used for analysis in accordance with an exemplary embodiment of the invention as illustrated in FIG. 2, but with a spaced reflective surface or mirror positioned to form an extended cavity [$\mathcal{L}$], so as to form a measuring device having a geometry which may be modified for the measurement of various physical stimuli or fixed so as to be used to analyze various gases (compounds).

Attention is directed to FIG. 3 of the drawings where the preferred semiconductor LASER 17 has its end surfaces provided with an appropriate measure of anti-reflection coating, one embodiment being a coating of necessary thickness formed of silicon monoxide 19. An external reflective surface (ERS) or mirror 20 is placed a distance parallel to one coated end surface 19 of the LASER cavity; and this mirror surface, which is coated for full or partial reflection, acts in cooperation with the cavity 17, providing the extended-LASER cavity 21.

A coherent light beam is transmitted out of cavity 17, the beam is reflected at the mirror 20 and back into the cavity 17. The interface depends on the degree of reflectivity of the anti-reflection coating at the cavity face fronting the mirror. This creates a standing wave between the external mirror and the far end of the LASER cavity; the silicon monoxide coating prevents lasing within the cavity length [l], and instead lasing occurs within the extended cavity length [$\mathcal{L}$] with the prevailing wave pattern extending over the length [$\mathcal{L}$].

Each gas, in the extended optical resonating cavity 21 will cause the extended-LASER cavity, with a cavity length [$\mathcal{L}$], to resonate at a unique frequency [$\mathcal{F}$], i.e., provided the sub-system is properly constructed, the standing wave pattern that can be supported by the cavity is a function of the cavity length and gas mixture at any given instant, and all other wave patterns will collapse. Methods to control/calibrate the variable cavity dimensions have been discussed in U.S. Pat. Nos. 4,983,035 and 4,930,134.

The extended-LASER cavity (ELC) sub-system is part of an integrated circuit that is controlled by microprocessor-based electronics 18, which also provide a system for analyzing the gases in the extended cavity 21. The microprocessor measures the basic operating frequency of the ELC, controls the port 16, cycles the ELC so that the sub-system is fast-tuned to a stable frequency, calibrates the sub-system for temperature drift and dimensional changes, and compares the frequency coded information for the gas mixture to a frequency spectrum provided in an electronic library for identification of gas type and concentration.

The frequency spectrum will be previously prepared by laboratory analyses for similar devices, and can be calibrated for each device according to the basic operating frequency of the ELC; which have been found linear with respect to temperature and dimensional differences. The tunable range in a GaAlAs LASER operating at a wavelength of about 8400 Angstroms is typically fifty to sixty Angstroms. Other types of LASERs may be used, depending on the type of gas mixture expected.

Once utilized, the device may be placed into a vacuum chamber for refurbishment, to facilitate the vacuum for calibration and operation for a new sample 11.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense. Further, it is noted that the appended drawings illustrate exemplary embodiments of this invention and are not to be considered limiting of the invention scope, for the invention may admit to other equally effective embodiments. Numerous variations and modifications will become apparent to those skilled in the art once the above disclosure is fully appreciated. It is intended that the following claims be interpreted to embrace all such variations and modifications.

What is claimed is:

1. The method of analyzing a fluid sample, comprising:
converting the fluid sample to gaseous state, thereby providing a gaseous sample;
providing a LASER having a body formed of active material capable of lasing, with first and second opposite ends,
said first end forming a first reflective surface, and
said second end having an anti-reflection coating and spaced therefrom an external reflective surface (ERS) so as to form an extended cavity therebetween;
said ERS positioned to reflect back into the extended cavity, thereby allowing formation of a standing wave between the reflective surfaces,
forming a vacuum in the extended cavity;
initiating the LASER, and establishing an initial operating frequency while the vacuum is present in the extended cavity;
inserting the gaseous sample into the extended cavity;
re-initiating the LASER, and establishing a secondary operating frequency while the gaseous sample is present in the extended cavity;
analyzing the results, thus determining the fluid sample's components and concentrations.

2. The method of claim 1 wherein converting the fluid sample into a gaseous state further comprises:
providing an evaporation chamber;
directing the fluid sample into the evaporation chamber; and
applying a thermal input to the fluid sample causing the fluid sample to enter a gaseous state.

3. The method of claim 2 further comprising:
controlling the thermal input so as to regulate the vaporization of the liquids, solid particles and markers that comprise the fluid sample.

4. The method of claim 3 further comprising:
filtering the gaseous sample of particles and markers such that the gaseous sample is a filtered gaseous sample.

5. The method of claim 4 wherein analyzing the results further comprises:
measuring the thermal input;
weighing the filter before filtering the gaseous sample;
weighing the filter after filtering the gaseous sample; and
determining the number and weight of the particles and markers captured by the filtering process.

6. The method of claim 4 wherein analyzing the results further comprises:
identifying markers filtered from the gaseous sample.

7. The method of claim 1, further comprising:
reheating the gaseous sample after filtering to maintain the sample's gaseous state.

8. The method of claim 1, wherein the operating frequency of the LASER is determined by:
producing a standing wave resonating within the LASER cavity.

9. The method of claim 1, wherein analyzing the results comprises a plurality of:
determining the change in the LASER operating frequency between the initial and secondary operating frequencies;
determining the markers present in the liquid sample; and
determining the number and weight of the solids in the liquid sample.

10. The method of claim 9, wherein analyzing the results further comprises:
comparing observed data to data observed from known samples.

11. The method of claim 9, wherein analyzing the results further comprises:
comparing observed data to known results in a database.

12. The method of claim 1, wherein said LASER comprises a GaAlAs device having a cavity length of about 300 microns and operating at a wavelength of about 8400 Angstroms.

13. The method of claim 1, wherein the liquid sample is blood.

14. The method of claim 1, wherein the liquid sample is urine.

15. A system for analyzing a fluid sample, comprising:
a LASER having first and second opposite ends;
said first end forming a first reflective surface; and
said second end having an anti-reflection coating and spaced therefrom an external reflective surface (ERS) so as to form an extended cavity therebetween;
said ERS positioned to reflect back into the extended cavity,
an input control device for adjusting the frequency of the LASER to produce a stable state;
means for producing a vacuum in the extended cavity; and
a port for controlling access to the extended cavity.

16. The system of claim 15 further comprising:
a liquid evaporation chamber;
a thermal input connected to the liquid evaporation chamber
a thermal input controller connected to the thermal input.

17. The system of claim 16 further comprising:
a filter between the liquid evaporation chamber and the control port.

18. The system of claim 17 further comprising:
a means for determining weight of the sample captured by a filter.

19. The system of claim 17 further comprising:
a means for counting particles of the sample captured by a filter.

20. The system of claim 17 further comprising:
a means for identifying markers of the sample captured by a filter.

* * * * *